United States Patent
Bauer et al.

(10) Patent No.: US 7,160,027 B2
(45) Date of Patent: Jan. 9, 2007

(54) MOTOR-ADJUSTABLE X-RAY SYSTEM

(75) Inventors: Jochen Bauer, München (DE);
Wendelin Feiten, Neubiberg (DE); Udo Heinze, Baiersdorf (DE); Martin Vierbücher, Ebern (DE)

(73) Assignee: Siemens Aktiengesellschaft, Munich (DE)

( * ) Notice: Subject to any disclaimer, the term of this patent is extended or adjusted under 35 U.S.C. 154(b) by 155 days.

(21) Appl. No.: 10/965,075

(22) Filed: Oct. 12, 2004

(65) Prior Publication Data
US 2005/0100134 A1 May 12, 2005

(30) Foreign Application Priority Data
Oct. 14, 2003 (DE) ................. 103 47 738

(51) Int. Cl.
*H05G 1/02* (2006.01)
(52) U.S. Cl. ............... 378/197; 378/193; 378/117; 318/2; 318/560
(58) Field of Classification Search ........... 378/193, 378/196, 197, 198, 117; 318/560, 567, 1, 318/2, 615
See application file for complete search history.

(56) References Cited

U.S. PATENT DOCUMENTS

| 5,671,266 A | | 9/1997 | Linhart ................ 378/175 |
| 6,045,262 A | * | 4/2000 | Igeta et al. ........... 378/209 |
| 6,409,381 B1 | * | 6/2002 | Siebenhaar et al. ..... 378/197 |

FOREIGN PATENT DOCUMENTS

DE 42 37 013 A1 5/1994

\* cited by examiner

*Primary Examiner*—Edward J. Glick
*Assistant Examiner*—Jurie Yun
(74) *Attorney, Agent, or Firm*—Brinks, Hofer, Gilson & Lione

(57) ABSTRACT

A motor-adjustable X-ray system comprises a C-arm, which has two degrees of freedom and is adjustable with a motor support. The motor support has a force pickup device which is provided to detect a force exerted by an operator when manipulating the C-arm. The force pickup device is configured to detect a plurality of directional components of the exerted force and to cooperate with an evaluation unit, by which as a function of the plurality of the directional components of the exerted force, different amounts of motor support of the C-arm in the two degrees of freedom are established via the evaluation unit.

18 Claims, 3 Drawing Sheets

MOTOR-ADJUSTABLE X-RAY SYSTEM

FIELD OF THE INVENTION

The invention relates to X-ray systems, and in particular to a motor-adjustable X-ray system with a C-arm that is adjustable with a motor support and has two degrees of freedom. The motor-adjustable X-ray system has a force pickup device provided to detect a force exerted by a user when adjusting or manipulating the C-arm.

BACKGROUND OF THE INVENTION

One such X-ray system is known for instance from German Patent Disclosure DE 42 37 013 A1. In order to select and unselect adjustable axes of a C-arm of an X-ray system, in particular for medical applications, typically a plurality of buttons is provided. These buttons are either spatially separated from the C-arm or, as in the X-ray system known from DE 42 37 013 A1, are moved together with the C-arm, giving the user an impression that he is moving the X-ray system with substantially smaller masses or lesser moments of inertia. A servo support of the C-arm thus provided may allow an adjustment using only slight user forces, but precisely this ease of motion of the C-arm may also have potentially a risk of adjustment in an unintended way.

OBJECT AND SUMMARY

The present invention is defined by the appended claims. This description summarizes some aspects of the present embodiments and should not be used to limit the claims.

One object is to disclose a motor-adjustable X-ray system which has a C-arm that is adjustable in at least two degrees of freedom and that can be adjusted in a desirable and convenient way and with substantially little risk of incorrect operation.

The X-ray system has a C-arm with two degrees of freedom, typically an angulation or curvature angle and an orbital angle. In addition, still other adjustment capabilities may be provided, such as a height adjustment. A motor drive mechanism is provided to adjust the C-arm in the two degrees of freedom; a force pickup or sensor device, which is desirably but not necessarily disposed on the C-arm, may detect a force exerted by the user to generate a signal for adjusting the C-arm, for instance for setting an angular speed or an acceleration. The force pickup device is embodied to detect a plurality of directional components of the force exerted by the user simultaneously, from which the direction in which the C-arm is to be adjusted is found. To enable substantially simple, intuitive use, a direction in which the user exerts a force on the force pickup device desirably at least approximately matches a direction in which the C-arm is to be adjusted. This may be done in the case where the force pickup device is disposed on the C-arm.

The force pickup device may cooperate with an evaluation unit, which as a function of a distribution of the directional components of the force exerted by the user, may establish various degrees of motor support of the C-arm in the various degrees of freedom. A primary component of the force transmitted by the user to the force pickup device may fix an axis, namely either an angular axis or an orbital axis, in which a reinforced servo support of the C-arm may take place, compared to the respective other axis. For the other axis, the servo support may be reduced, or omitted, or a braking action on the C-arm and in particular blocking of the C-arm may be provided. In this last case, the adjustability of the C-arm may thus be fixed strictly to one degree of freedom. A possibility of varying the motor support of the C-arm in various degrees of freedom, which exists because of the type of actuation of the force pickup device, or specifically the distribution of the directional components of the user force, is realized by providing that sensor characteristic curves of force and/or travel pickups of the force pickup device are modified, in particular made flatter or wider.

A selection of the particularly desirable degree of freedom in which a reinforced motor support takes place may remain unchanged during one complete adjustment operation of the C-arm. As such, the choice thus made of an adjustment direction may remain operative, limited or fixed at least temporarily, even beyond the adjustment operation. Accordingly, when a second adjusting motion is initiated by the user and is affected particularly with only a slight temporal or chronological spacing or time delay from the first adjusting motion, it is assume that the user is intending to make a further adjustment, for instance for correcting the first motion, either in or opposite the direction selected for the first motion. For a chronologically limited fixation of the adjustment direction of the motor support, a memory unit is provided, and the time interval during which the adjustment direction is maintained is variable by the user and/or by user control parameters, such as the duration or the travel distance of an adjustment operation.

In one feature, the X-ray system has a user control handle disposed on the C-arm, which in cooperation with at least one force pickup device, may simultaneously detect the various directional components of the user force. Hence the C-arm can be conveniently adjusted using only one hand.

If one of the degrees of freedom of the C-arm is fixed as a degree of freedom with reinforced motor support, then the user may nevertheless be capable of easily canceling or changing the desirable adjustment direction. As such, a separate input device may for instance be provided. As an alternative or in addition, a possibility is provided of canceling the restriction, in particular the blocking, of the C-arm in the second adjustment direction by exerting a force that is above a threshold, in particular a settable threshold, exerted on the force pickup device in the applicable direction.

The object may also be attained by a method for motor adjustment of a C-arm of an X-ray system. All, some or none of the advantages and refinements of the X-ray system named in conjunction with the equipment may apply logically to the method as well, and vice versa.

In another advantageous feature, for a choice of a desirable direction of a servo support of a C-arm of an X-ray system as a function of the force exerted by the user, a dynamic axis locking is provided. This axis locking can desirably be selected and unselected as a user control option by the user.

Illustrative and exemplary embodiments of the invention are described in further detail below with reference to and in conjunction with the figures.

BRIEF DESCRIPTION OF THE DRAWINGS

Parts and parameters corresponding to one another are identified by the same reference numerals in all the drawings.

DETAILED DESCRIPTION OF THE PREFERRED EMBODIMENTS

Figure 1A:
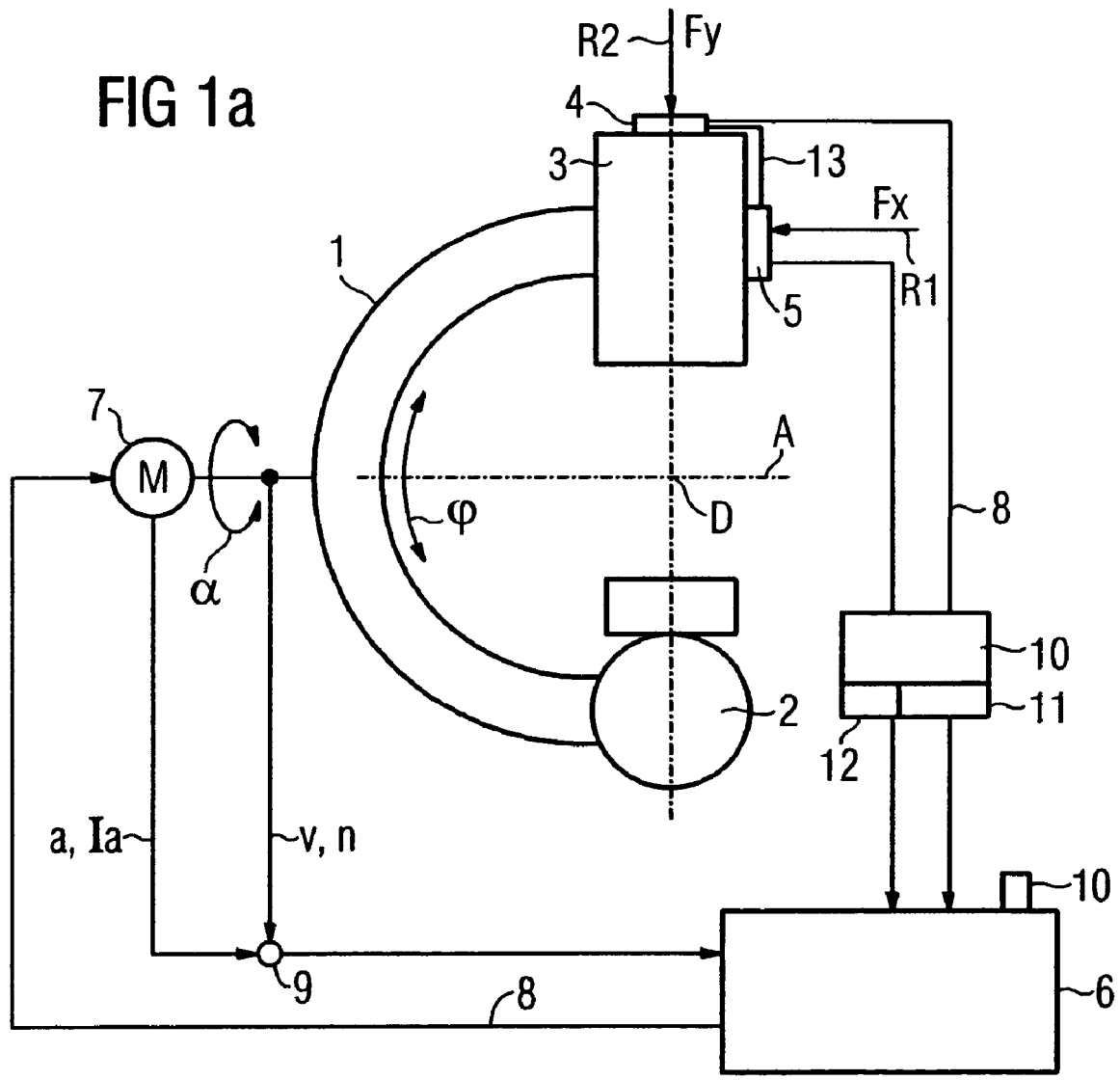
FIG. 1a illustrates schematically an X-ray system with a motor-adjustable C-arm in one embodiment.
Figure 1B:
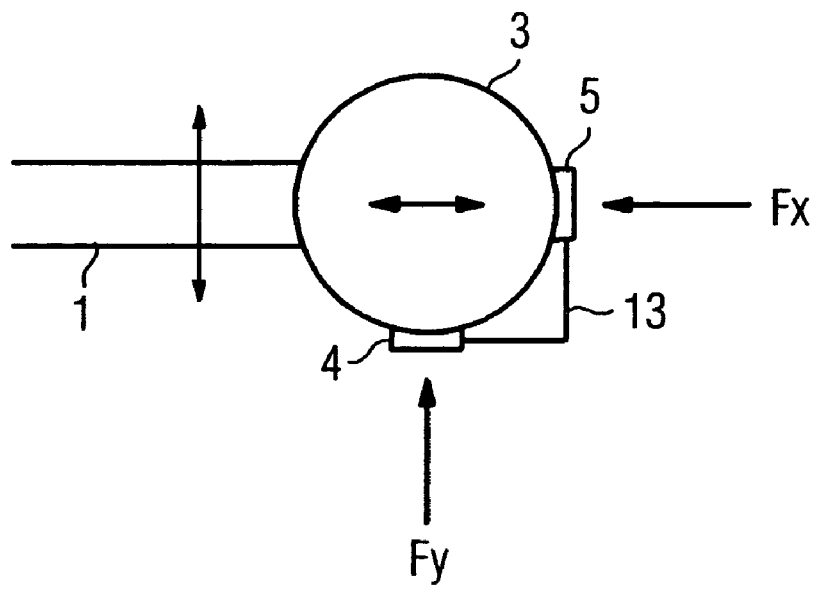
FIGS. 1b and 1c illustrate schematically one embodiment of an X-ray image amplifier with force pickups disposed thereon.
Figure 1C:
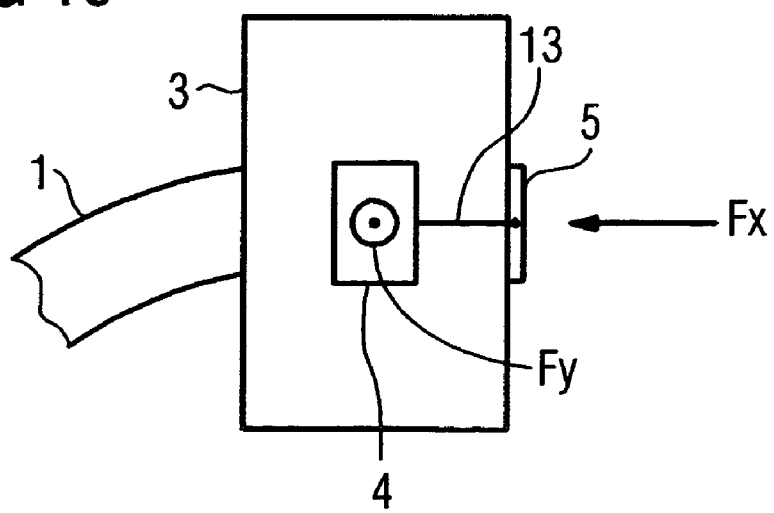

FIG. 1a, schematically, shows an X-ray system, which has a C-arm 1 that is adjustable in two degrees of freedom, defined by an angulation or curvature angle α and an orbital angle φ. An axis about which the C-arm 1 is angularly adjustable is marked A, and a pivot point about which the C-arm is rotatable in the orbital direction is marked D. An X-ray source or emitter 2 is disposed on one end of the C-arm 1, and an X-ray image amplifier 3 is disposed on the other end. For the motor-supported adjustment of the C-arm 1 including the X-ray source 2 and the picture-taking system 3, two force pickups or sensors 4, 5 forming a force pickup device are provided, which are actuatable by an essentially curved or angled user control handle 13. In an alternate embodiment, desirably a plurality of user control handles 13, also known as servo railings, is disposed on the C-arm 1. The force which is exerted on the user control handle 13 may determine the adjustment direction of the C-arm 1. In this schematic view of FIG. 1a, the force components of the force, which can be exerted by the user on the force pickup device 4, 5 by means of the user control handle 13, are marked Fx and Fy, and the associated directional components are marked R1 and R2. The orbital angle φ can be adjusted via the force component Fx in the direction R1; the angulation angle α can be adjusted via the force component Fy, which in the position of the C-arm 1 shown may act perpendicular to the plane shown. In the perspective views of FIGS. 1b and 1c, the X-ray image amplifier 3 can be seen in detail with the force pickups 4, 5. A capability of adjusting the C-arm 1 in the orbital and angulation directions is represented in FIG. 1b by double arrows.

Control signals may be sent from the force pickup device 4, 5 via lines 8, or wirelessly, via an evaluation unit 10 to a closed-loop control unit 6; the evaluation unit 10 may also be integrated with the closed-loop control unit 6. With the aid of the evaluation unit 10, the directional component R1 or R2 in which the user force is predominantly exerted on the force pickup device 4, 5 may be ascertained, or in other words, whether an adjustment of the orbital angle φ or of the angulation angle α of the C-arm 1 is being initiated. A further adjustment of the C-arm 1 may then be restricted, in the manner of a dynamic axis locking, to the adjustment direction α, φ selected by the initiation of the adjusting motion. Thus, the capability of adjusting the C-arm 1 during the adjusting motion is reduced from two degrees of freedom to one degree of freedom. As such, a need of the user may be met; who operationally may not intend to perform a simultaneous angular and orbital adjustment of the C-arm 1 but instead may intend only to perform an angular adjustment or only an orbital adjustment, in a defined way. Alternately, the function of the dynamic axis locking can be cancelled at any time via the closed-loop control unit 6.

The closed-loop control unit 6 may serve to trigger a plurality of motors, of which as an example an electric motor 7 is shown with which the C-arm 1 is adjustable. Via a comparator 9 and lines 8, the closed-loop control unit 6 may be supplied with signals pertaining to an acceleration a of the X-ray system 1, 2, 3; an armature current Ia of the electric motor 7; a speed v of the X-ray system 1, 2, 3; and the rpm n of the electric motor 7.

Figure 2:
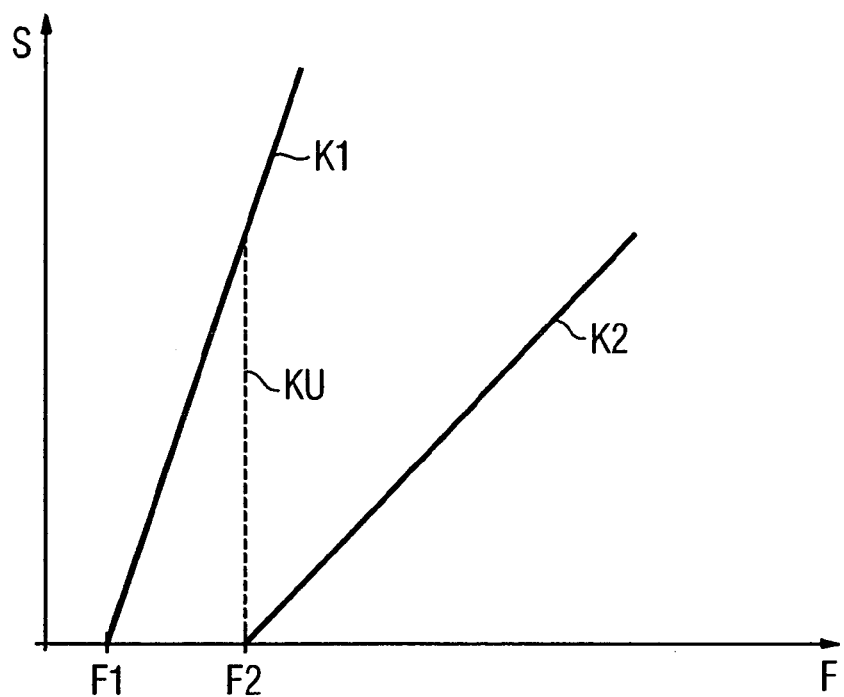
FIG. 2 is schematic graph of the variable motor-adjustment of the C-arm of the X-ray system of FIGS. 1a through 1c.

A memory unit 11 is integrated inside the evaluation unit 10, for storing various characteristic curves K1, K2 (as shown in FIG. 2) in memory; these characteristic curves may each fix the servo support in the respective adjustment directions α, φ. The memory unit 11 may also cooperate with a delay switch 12, realized for instance by software, which may assure that the adjustment direction α, φ selected during an adjustment operation of the C-arm 1 may also remain activated as a adjustment direction α, φ even after a conclusion of the adjustment operation.

In FIG. 2, a plurality of characteristics of the motor support of the C-arm 1 that is adjustable by means of the force pickup device 4, 5 and the evaluation unit 10 cooperating with it is shown in a graph. The user may exert a force F, or in other words the force components Fx and Fy on the force pickup 5 and the force pickup 4, respectively. An action exerted as a function of the exerted force F by the motor 7 may be designated as the servo force S, which may pertain only to one of the force components, either Fx or Fy. If the direction in which the force F is exerted is equivalent to the adjustment direction α, φ of the C-arm 1 that has been set as the desirable direction, then a first characteristic curve K1 is activated. If, before the adjustment operation begins, neither of the adjustment directions α, φ has been set as the desirable direction, then the desirable adjustment direction α, φ of the C-arm 1 is obtained from the direction in which the adjustment of the C-arm 1 is initiated, or in other words on the basis of which one of the directional components R1, R2 predominates when the adjustment operation is initiated.

As long as the force F is below a low, first force threshold F1, the C-arm 1 is not put into motion. When the first threshold F1 is exceeded, the servo support is put into force (that is, a relatively high servo S is attainable via a relatively slight user force F). For the second adjustment direction φ, α, a second characteristic curve K2 is operative during the thus-initiated adjustment operation and for a settable length of time beyond it. As long as the force F exerted for adjusting the C-arm 1 in the second adjustment direction φ, α does not exceed a second threshold F2, a motion in the second adjustment direction φ, α continues to be precluded. Not until this second threshold F2 is "overtaken" is an adjustment of the C-arm 1 also possible in the second adjustment direction φ, α. However, in comparison to the first characteristic curve K1, the second characteristic curve K2 has a substantially lesser slope, so that the servo support is less in the second adjustment direction φ, α. In an alternative feature, it is provided, as indicated by a transition characteristic curve KU shown in dashed lines, that the inhibition or restricted blocking pertaining to the second adjustment direction φ, α be cancelled upon overtaking of the second threshold F2, and a shift to the first characteristic curve K1 may be made.

Figure 3:
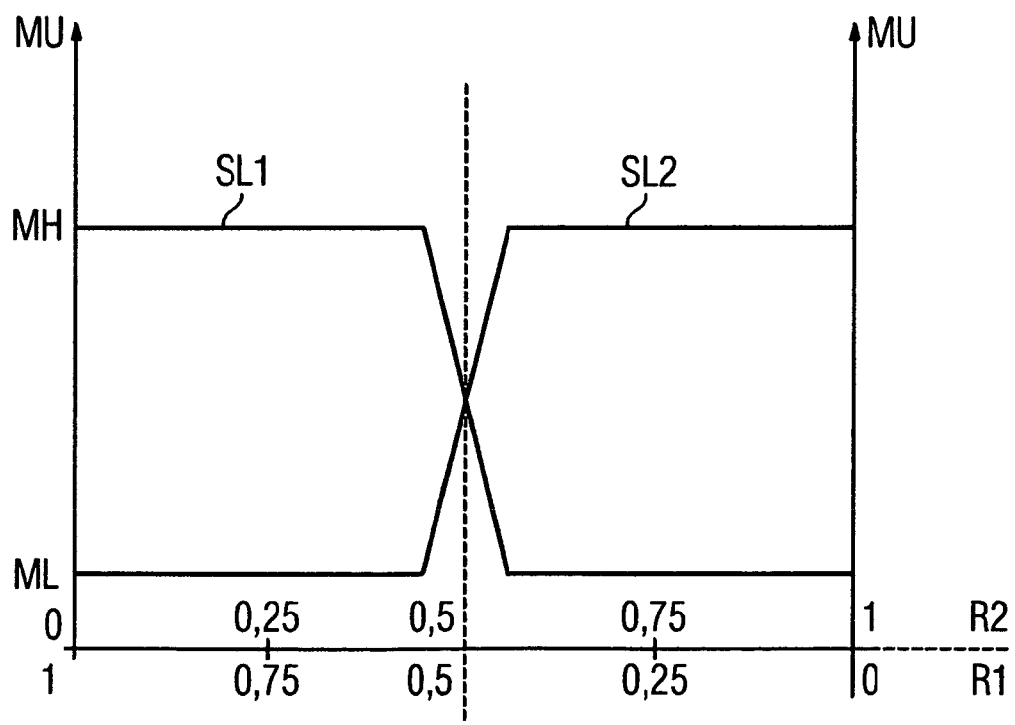
FIG. 3 is a schematic graph of the dependency of the servo support with respect to various degrees of freedom of the directional components of a user force acting on a force pickup device in one embodiment.

A dependency of the motor support MU of the C-arm 1 on the allocation of the user force F to the force components Fx, Fy is also illustrated in FIG. 3. The force F is operative in arbitrary proportions in the directional components R1 and R2, and the sum of the two directional components R1, R2 is always 1. The directional components R1, R2 pertain to the angles between the user force F and the directions in space in a coordinate system, rather than to the amounts of the force components Fx, Fy. For instance, if the angle between the force vector, that is, the user force F, and the X axis is 30°, and the angle between the force vector and the Y axis is 60°, then the angle of the force vector with respect to the axes is equivalent to a directional component R1 of ⅔ and a directional component R2 of ⅓. If, as in this case, the directional component R1 on the left in the graph predominates, then a first switching line SL1, which may pertain to the adjustment of the orbital angle φ of the C-arm 1, is set to a maximum support level MH. Here, the characteristic curve K1 of FIG. 2 is activated. Simultaneously, the motor support MU pertaining to the second adjustment direction, that is, the angulation angle α, is set to a minimum support level ML, such as shown by the characteristic curve K2 of FIG. 2.

Conversely and analogously, in accordance with a second switching line SL2, the motor support MU in the direction of the angulation angle α is desired if when the adjusting motion is initiated the force component Fy and thus the directional component R2 predominate. If during the adjustment operation of the C-arm 1 the allocation of the directional components R1, R2 of the force F changes, then, at least as long as the second threshold F2 is not exceeded, the fixation of the desirable adjustment direction α, φ does not change. Thus, the adjustment of the C-arm 1 takes place along a path that can be realized by control technology and that enables solely an adjustment in the direction of the angulation angle α or in the direction of the orbital angle φ.

The invention claimed is:

1. A motor-adjustable C-arm X-ray system comprising:
a C-arm which has two degrees of freedom and is adjustable with motor support;
a force pickup device operable to detect a force exerted by an operator when manipulating the C-arm, wherein the force pickup device is operable to detect a plurality of directional components of the exerted force; and
an evaluation unit which, as a function of the plurality of the directional components of the exerted force, establishes different amounts of motor support of the C-arm in the two degrees of freedom,
wherein the two degrees of freedom are an angulation angle and an orbital angle of the C-arm.

2. The X-ray system of claim 1, wherein the evaluation unit is configured as an axis locking device that locks an adjustment of the C-arm into one degree of freedom.

3. The X-ray system of claim 2, further comprising a memory unit operable to store characteristic curves pertaining to the motor support of the C-arm, the characteristic curves being determined by an allocation of the directional components of the exerted force.

4. The X-ray system of claim 2, wherein a plurality of directional components of the force exerted by the operator is detectable by the force pickup device with a single user control handle.

5. The X-ray system of claim 1, further comprising a memory unit operable to store characteristic curves pertaining to the motor support of the C-arm, the characteristic curves being determined by allocation of the directional components of the exerted force.

6. The X-ray system of claim 5, further comprising a delay switch operable to temporarily delay a fixation of the motor support adjustment of the C-arm.

7. The X-ray system of claim 6, wherein a plurality of directional components of the force exerted by the operator is detectable by the force pickup device with a single user control handle.

8. The X-ray system of claim 5, wherein a plurality of directional components of the force exerted by the operator is detectable by the force pickup device with a single user control handle.

9. The X-ray system of claim 1, further comprising a memory unit operable to store characteristic curves pertaining to the motor support of the C-arm, the characteristic curves being determined by an allocation of the directional components of the exerted force.

10. The X-ray system of claim 1, wherein a plurality of directional components of the force exerted by the operator is detectable by the force pickup device with a single user control handle.

11. The X-ray system of claim 1, wherein a plurality of directional components of the force exerted by the operator is detectable by the force pickup device with a single user control handle.

12. A method for motor adjustment of a C-arm of an X-ray system, the C-arm having two degrees of freedom, in which an adjustment operation of the C-arm is effected as a function of a force transmitted by a user to a force pickup device, the method comprising:
detecting a direction of the force which the user exerts to adjust the C-arm;
determining a predominant directional component from two directional components of the exerted force; and
motor-supporting as a function of the predominant directional component the adjustment operation of the C-arm in a first adjustment direction to an increased level compared to a second adjustment direction.

13. The method of claim 12, further comprises:
blocking an adjustment of the C-arm in the second adjustment direction to at least a limited extent during the adjustment of the C-arm in the first adjustment direction.

14. The method of claim 13, further comprises rescinding the blocking of the C-arm in the second adjustment direction when a force exerted by the user for the second adjustment direction exceeds a threshold.

15. The method of claim 14, further comprises automatically selecting an amplified motor support of the C-arm in the first adjustment direction to the increased level even in a later adjustment operation within a determined time interval, regardless of which one of the two directional components of the force exerted by the user predominates.

16. The method of claim 13, further comprises automatically selecting an amplified motor support of the C-arm in the first adjustment direction to the increased level even in a later adjustment operation within a determined time interval regardless of which one of the two directional components of the force exerted by the user predominates.

17. The method of claim 12, further comprises automatically selecting an amplified motor support of the C-arm in the first adjustment direction to the increased level even in a later adjustment operation within a determined time interval regardless of which one of the two directional components of the force exerted by the user predominates.

18. The method of claim 17, wherein the determined time interval is adjustable.

* * * * *